United States Patent [19]

Nakajima et al.

[11] Patent Number: 4,486,311

[45] Date of Patent: Dec. 4, 1984

[54] METHOD FOR EFFECTIVE COMBINED USE OF GELS HAVING DIFFERENT ACTIVITIES

[75] Inventors: Shigeru Nakajima, Okayama; Masahiko Ozaki, Ootsu, both of Japan

[73] Assignee: Japan Exlan Company Limited, Osaka, Japan

[21] Appl. No.: 589,044

[22] Filed: Mar. 14, 1984

Related U.S. Application Data

[63] Continuation of Ser. No. 464,066, Feb. 4, 1983, abandoned.

[30] Foreign Application Priority Data

Feb. 23, 1982 [JP] Japan ................................. 57-28598

[51] Int. Cl.$^3$ .............................................. B01N 15/08
[52] U.S. Cl. ..................................... 210/635; 210/658
[58] Field of Search .................................. 210/635, 656

[56] References Cited

U.S. PATENT DOCUMENTS 3,580,843  5/1971  Salyer et al. ..................... 210/635
4,301,139  11/1981  Feingers et al. .................. 210/656
4,314,823  2/1982  Rich et al. ........................ 210/656

*Primary Examiner*—John Adee
*Attorney, Agent, or Firm*—Wenderoth, Lind & Ponack

[57]            ABSTRACT

In packing gels of different activities together into a liquid chromatographic column, this invention provides a method which makes it possible to obtain a remarkably elevated separation performance by packing a gel of high activity in a layer at the outlet side of the column for a length within the range of 5 to 60% of the total packing length.

4 Claims, No Drawings

METHOD FOR EFFECTIVE COMBINED USE OF GELS HAVING DIFFERENT ACTIVITIES

This application is a continuation of now abandoned application Ser. No. 464,066, filed Feb. 4, 1983.

BACKGROUND OF THE INVENTION

1. Field of the Invention

The present invention relates to a method of packing gels of different activities together into a liquid chromatographic column.

2. Description of the Prior Art

In recent years, liquid chromatography has been used not only as an analytical means but also as one of the separation means in many fields such as food industry, medical product industry, chemical industry including purification and synthesis of intermediate products, inorganic industry, fiber industry, etc. In such industrial fields, since a large quantity of expensive gels are packed into enormous columns, it is very important to maintain the life of the gels in the columns for a long time. But after a long period of operation in liquid chromatography, impurities accumulate in the columns, and the gel layer near the inlet of the columns is severely contaminated. This lowers the separation performance of the columns and further reduces the treating capacity, causing industrial problems such as an increase in pressure loss, damage of the filter in the columns, etc. Therefore, in order to prevent the occurence of such problems, it is desirable to change the whole quantity of the gel before the contamination becomes severe. However, since such a method consumes a large amount of expensive gels, a means is generally employed wherein only the severely contaminated gel portion near the inlet of the column is discarded and the column is packed again with a mixture of the remaining gel and supplemental high activity gel, or a means is employed wherein the contaminated gel portion is replaced by a high activity gel is employed at the inlet side of the column is employed. Particularly, the gel near the inlet of the column is remarkably contaminated in comparison with the gel at the center or near the outlet, and also the effect of a broadened or distorted peak which may occur near the inlet of the column carries over to the final stage. Therefore, it is believed that, with any contrivance given to the gel layer in the central part or near the outlet, no improvement of the separation performance can be attained. Accordingly, it is customary practice to use the means of supplementing a high activity gel to the inlet side of the column.

SUMMARY OF THE INVENTION

Under such circumstances, we carried on a further study and as a result, it has been found that, contrary to what has been believed in the field of industry concerned, the performance of the gel at the outlet side of the column greatly governs the separation performance of the whole column. The present invention is based on this discovery.

Therefore, in packing gels of different activities together into a liquid chromatographic column, an object of the present invention is to provide a method which can effectively elevate the separation performance of the column. Another object of the invention is to provide a method of gel supplementation which can remarkably elevate the separation performance of the column as a whole with the least amount of an expensive gel. Other objects of the invention will become apparent from the following concrete explanation of the invention.

The above-mentioned objects of the present invention are attained by packing a high activity gel in a layer at the outlet side of the column for a length within the range of 5 to 60% of the total packing length.

DETAILED DESCRIPTION OF THE INVENTION

First, as for the gels to be used in carrying out the present invention, there is no particular limitation, so far as they are gels for liquid chromatographic use, and there can be mentioned those gels for use in liquid chromatography such as gels for molecular sieve chromatography, partition chromatography, adsorption chromatography, ion-exchange chromatography, etc.

The term "high activity gel" as used in the present invention means a gel having the highest separation performance among the two or more gels to be packed into the same column and having different brands or histories, and such gels, in contrast to a gel having a low separation performance (in most cases old gels), include for example a fresh gel of the same brand, a purified, regenerated product from a contaminated gel, a gel of a different brand and having a higher separation performance, etc.

The amount of such a high activity gel to be used should be determined so as to be within the range of from 5 to 60%, preferably from 10 to 40%, based on the total packing length of the gels packed into the column in a swollen state. If the ratio of the gel is below the lower limit of the range, there will be no substantial effect of packing the high activity gel. If the ratio exceeds the upper limit of the range, the performance will be approximate to that of the case of mixed use, and moreover the use of such a large amount of the expensive gel should be avoided. It is necessary that the high activity gel to be used in such a ratio should be packed in a plane and nearly at right angles to the direction of the flow of the liquid which passes through the column. If this requirement is not satisfied, the peak will be broadened to lower the separation performance.

In the following, there will be described how the gel of high activity is packed and arranged at the outlet side of a column. In one method, which is applicable to a fixed type column, the direction of the liquid fed to the column from the upper end or the lower end is selected so that the packed layer of the high activity gel should be positioned at the outlet side of the column. In another method, in which the column can be set either uprightly or inversely, the direction of the liquid fed to the column and the direction of fixing the column body are selected so that the packed layer of the high activity gel should be positioned at the outlet side of the column.

The kind of developing solvent is suitably selected in conformity with the purpose of separation, properties of the gel, etc., and is not limited in carrying out the present invention.

As regards the column in which such a gel is to be packed, there is no limitation. However, when using a large diameter column for industrial use, a particularly pronounced effect is obtained. Thus, it is desirable to use a column having an inner diameter larger than 10 cm, preferably larger than 20 cm. Also, it is desirable to use a column having a length greater than 20 cm, preferably longer than 30 cm.

We do not exactly understand why the method of the present invention can improve the separation performance markedly in comparison with the method wherein the column is packed again with a mixture of the gel remaining after the removal of the contaminated gel portion and supplemental high activity gel, or a method wherein, in place of the contaminated gel portion, a high activity gel is supplemented at the inlet side of the column. But we suppose that, regardless of how the separation may be carried out with a high activity gel at the earlier stage (i.e. at the inlet side of the column), when the liquid passes through a gel layer of inferior separation performance at a later stage, it is the performance of the gel in the later stage which exerts a dominant influence on the final separation performance.

It is an effect of the present invention worthy of special mention that it is possible to promote the separation performance of the column as a whole by supplementing a small amount of a high activity gel, and the invention has made it possible to prolong the useful life of the most part of the gel which has become less active in separation performance, by supplementing a small amount of a high activity gel.

It is also an industrial advantage of the present invention that it has made it possible to supplement the gel by a simpler operation than the method of using a mixture wherein the remaining gel in the column is taken out, mixed with supplemental gel and then the mixture is packed again into the column.

In the following, the present invention will be explained in more detail by way of examples, but it is to be understood that the invention is not limited by the description of these examples. All percentages are by weight unless otherwise indicated.

The gel activity (%) as described in the following examples is measured and calculated by the following method:

A gel to be evaluated is packed almost up to the highest density into a column having an inner diameter of 1.5 cm and a height of 30 cm. Into this column, 250 ml of a 5% aqueous solution of sodium thiocyanate is poured. Then, as the eluent, pure water at 35° C. is caused to flow at the rate of 1 ml/min. An elution curve is obtained using a differential refractometer (produced by Laboratory Data Control Inc.) as the detector. By subtracting the volume (ml) of the interstices among the gel particles from the eluted volume of NaSCN at the peak position on the elution curve, a value is obtained which is the net volume of eluted NaSCN (Ve ml). In the same way, the net volume of eluted NaSCN when the column is packed with particles of a fresh gel (Vs ml) is obtained. The gel activity is calculated by the following formula:

Gel activity (%)=(Ve/Vs)×100

The nearer this value to 100, the nearer is the separation performance (adsorption and elution) of the gel to that of fresh gel.

EXAMPLE 1

In a wet-spinning process for producing acrylic fibers in which a concentrated aqueous solution of NaSCN was used as the solvent, a contaminated gel (Sephadex G-10) which had been used for 5 years in the purification process of said solvent and had become less active in separation performance, was decantation-treated with water three times and then filtered by suction to prepare a contaminated gel for evaluation (a component of composite gels to be evaluated in the following experiments).

The composite gels composed of this contaminated gel and fresh gel of the same kind as the contaminated gel were packed into columns in the ratios described in Table 1, (A) as a mixture, (B) with the fresh gel positioned at the inlet side of the column, and (C) with the fresh gel positioned at the outlet side of the column. The composite gels were measured for their gel activity (%), which is also described in Table 1.

TABLE 1

| Composite gel for evaluation No. | Percentage of the fresh gel packed (%) | Packing method | Gel activity (%) |
|---|---|---|---|
| 1 | 65 | A | 88 |
| 2 | 65 | C | 89 |
| 3 | 50 | A | 82 |
| 4 | 50 | B | 78 |
| 5 | 50 | C | 85 |
| 6 | 40 | A | 79 |
| 7 | 40 | B | 74 |
| 8 | 40 | C | 82 |
| 9 | 20 | A | 72 |
| 10 | 20 | B | 70 |
| 11 | 20 | C | 76 |
| 12 | 10 | A | 69 |
| 13 | 10 | B | 68 |
| 14 | 10 | C | 72 |
| 15 | 4 | A | 68 |
| 16 | 4 | B | 67 |
| 17 | 4 | C | 68 |
| 18 | 0 | — | 67 |

Note:
The marks indicate experiments of the invention.

As apparent from the results in Table 1, it is understood that the method of the present invention elevates the separation Performance more effectively than the conventional methods, even if the packed amount of the high activity gel is the same.

EXAMPLE 2

Composite gels to be evaluated were prepared and arranged in the same way as in Example 1 except that a gel (Sephadex G-25) which had been used in the demineralization process of dextran for two years and had become less active in separation performance was used. The activity of the composite gels was measured. The results are shown in Table 2.

TABLE 2

| Composite gel for evaluation No. | Percentage of the fresh gel | Packing method | Gel activity (%) |
|---|---|---|---|
| 1 | 40 | A | 79 |
| 2 | 40 | B | 75 |
| 3 | 40 | C | 82 |
| 4 | 20 | A | 73 |
| 5 | 20 | B | 70 |
| 6 | 20 | C | 77 |
| 7 | 0 | — | 68 |

Note:
The marks indicate experiments of the present invention.

It will be understood that, by employing the method of the present invention, the separation performance can be effectively elevated.

What is claimed is:

1. A method of improving the separation performance of a column packed with a contaminated gel for liquid chromatography, said column having an inlet and an outlet for a liquid, which comprises removing the contaminated gel from the outlet side of said column for a length of 5 to 60% of the total packed length of said column, and packing the resultant void in said column with a fresh gel of the same type of activity, but higher activity, compared to the contaminated gel remaining in said column.

2. The method as claimed in claim 1 wherein the inner diameter of the column is larger than 10 cm.

3. The method as claimed in claim 1 wherein the length of the column is greater than 20 cm.

4. A method of conducting liquid chromatography after improving the separation performance of a column packed with a contaminated gel for liquid chromatography, said column having an inlet and an outlet for a liquid, which comprises removing the contaminated gel from the outlet side of said column for a length of 5 to 60% of the total packed length of said column, packing the resultant void in said column with a fresh gel of the same type of activity, but higher activity, compared to the contaminated gel remaining in said column, and introducing a liquid to be subjected to chromatography into the inlet of said column.

* * * * *